(12) United States Patent  
Malowaniec

(10) Patent No.: US 8,202,390 B2
(45) Date of Patent: Jun. 19, 2012

(54) METHOD FOR THE PRODUCTION OF AN ABSORBENT DISPOSABLE INCONTINENCE DIAPER

(75) Inventor: Krzysztof D. Malowaniec, Heidenheim (DE)

(73) Assignee: Paul Hartmann Aktiengesellschaft, Heidenheim (DE)

( * ) Notice: Subject to any disclaimer, the term of this patent is extended or adjusted under 35 U.S.C. 154(b) by 372 days.

(21) Appl. No.: 12/607,698

(22) Filed: Oct. 28, 2009

(65) Prior Publication Data

US 2010/0108251 A1 May 6, 2010

Related U.S. Application Data

(60) Provisional application No. 61/193,311, filed on Nov. 17, 2008.

(30) Foreign Application Priority Data

Nov. 6, 2008 (DE) .......................... 10 2008 056 220

(51) Int. Cl.
*B32B 37/00* (2006.01)
*B32B 37/02* (2006.01)
*B32B 38/00* (2006.01)
*B32B 38/04* (2006.01)
*B32B 38/10* (2006.01)

(52) U.S. Cl. ........ 156/253; 156/250; 156/252; 156/256; 156/259; 156/267; 156/269

(58) Field of Classification Search .................. 156/250, 156/252, 253, 256, 259, 267, 269, 510, 516, 156/518–521; 604/385, 385.21, 385.24, 604/385.25

See application file for complete search history.

(56) References Cited

U.S. PATENT DOCUMENTS

| | | | | |
|---|---|---|---|---|
| 5,705,013 A * | 1/1998 | Nease et al. | .................. | 156/260 |
| 6,820,671 B2 * | 11/2004 | Calvert | .......................... | 156/543 |
| 2004/0108054 A1 * | 6/2004 | Otsubo et al. | .................. | 156/259 |
| 2007/0267149 A1 * | 11/2007 | McCabe | ....................... | 156/584 |

FOREIGN PATENT DOCUMENTS

EP 1915977 4/2008

\* cited by examiner

*Primary Examiner* — Mark A Osele
*Assistant Examiner* — Christopher C Caillouet
(74) *Attorney, Agent, or Firm* — Brinks Hofer Gilson & Lione

(57) ABSTRACT

We disclose a method for the production of a diaper, with an absorbent body, a front portion, a back portion and a crotch portion arranged in-between, and with lateral back portions bilaterally attached to the back portion and lateral front portions bilaterally attached to the front portion, which extend in transverse direction of the diaper beyond the main body, and are spaced apart in the longitudinal direction of the diaper, where the lateral back and front portions may be detachably connected to one another to apply the diaper, where a separation process including the lateral back portion, the main part and the lateral front portion is implemented to contour the bilateral leg opening areas of the diaper, so that a connected offcut is formed, characterized in that the offcut is gripped and conveyed away by a transfer roller having pin-, needle-, knob-, hook- or barb-shaped mechanical elements protruding from its surface.

13 Claims, 8 Drawing Sheets

METHOD FOR THE PRODUCTION OF AN ABSORBENT DISPOSABLE INCONTINENCE DIAPER

CROSS-REFERENCE TO RELATED APPLICATIONS

Figure 1:
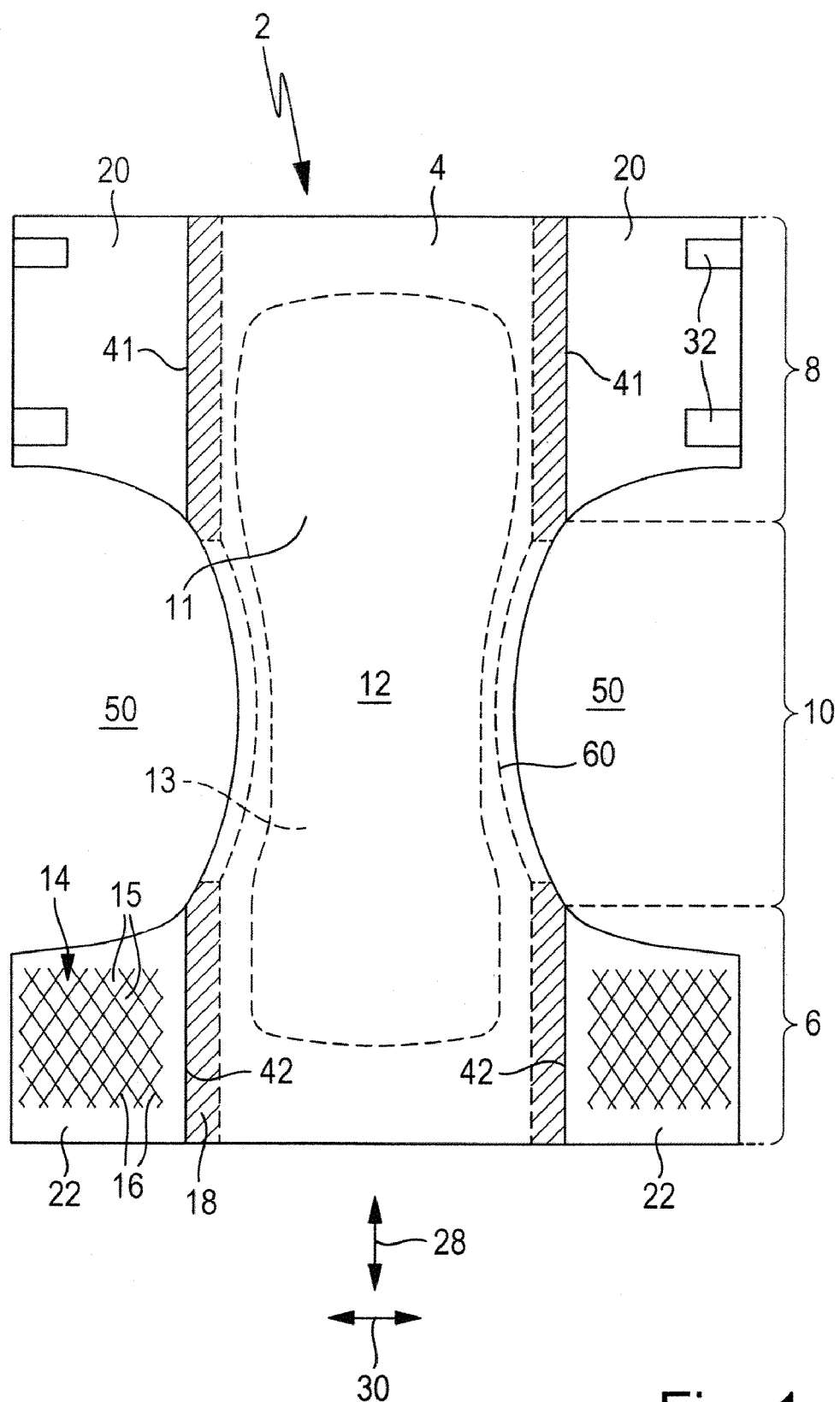

This application claims the benefit of German Application No. 10 2008 056 220.3, filed Nov. 6, 2008 and U.S. Provisional Application No. 61/193,311 filed Nov. 17, 2009. The disclosures of the above applications are incorporated herein by reference.

FIELD

The present disclosure relates to a method for the production of an absorbent disposable incontinence diaper of the open type.

BACKGROUND

The statements in this section merely provide background information related to the present disclosure and may not constitute prior art.

An absorbent disposable incontinence diaper of the open type may have a main part having an absorbent body, comprising a front portion with lateral longitudinal front edges, a back portion with lateral longitudinal back edges and a crotch portion arranged in between, located between the legs of the wearer, and having back side sections attached to both sides of the back portions and front side sections attached to both sides of the front portions, which extend in the transverse direction of the disposable incontinence diaper beyond the longitudinal front and/or back edges of the main part and are spaced apart from one another in the longitudinal direction of the disposable incontinence diaper, whereby the back and front side sections may be detachably connected to one another to apply the disposable incontinence diaper. Such an open-type disposable incontinence diaper and a method of production thereof is the subject matter of the not previously disclosed EP 07 015 141.0 by the applicant.

In disposable incontinence diapers of this type, said lateral portions are frequently made of a material that is different from the main part. The lateral portions which frequently are designated as "ears" of the disposable incontinence diaper, may, for example, be configured to be breathable, in particular air-pervious and/or water vapor-pervious, whereas the main part, which is frequently designated as the chassis, may be configured to be liquid-pervious. To close the disposable incontinence diaper, the lateral portions attached to the back portion are applied to the abdominal side of the wearer and detachably connected, either to the outside of the front portion of the main part or to the outside of the lateral portions of the front portion.

In order to increase the wear comfort of such disposable incontinence diapers, it has already been proposed in EP 07 015 141.0 to configure the leg opening areas of the disposable incontinence diaper to be contoured, for example in such a way that it is carried out—as already mentioned above—by a continuous or quasi continuous separation process, in particular by means of a cut or punching so that an even, continuous edge is formed.

SUMMARY

We disclose a method for the production of an absorbent disposable incontinence diaper of the open type, with a main part having an absorbent body, having a front portion with lateral longitudinal front edges, a back portion with lateral longitudinal back edges and a crotch portion arranged in between, located between the legs of the wearer, and having back side sections attached to both sides of the back portions and front side sections attached to both sides of the front portions, which extend in the transverse direction of the disposable incontinence diaper beyond the longitudinal front and/or back edges of the main part and are spaced apart from one another in the longitudinal direction of the disposable incontinence diaper, whereby the back and front side sections may be detachably connected to one another to apply the disposable incontinence diaper, whereby in order to contour both leg openings of the disposable incontinence diaper, a continuous or quasi continuous separation process respectively including the back lateral portion, the main part and the front lateral portion is carried out, so that a continuous offcut is formed by the back lateral portion, the main part and front lateral portion which must be conveyed away.

The separating line formed by the separation process in this case includes the lateral back portion, the main part and the lateral front portion. The leg opening areas are thus exclusively formed by cutting or separating lines of the single, continuous or quasi-continuous separation process which implies an economic production of the disposable incontinence diaper and improves the wear comfort of the disposable incontinence diaper. The contours of the leg opening areas may comprise straight, in particular oblique, sections to the longitudinal direction of the disposable incontinence diaper and/or curved sections. In a variation, the contour of the leg opening areas has curved sections. The minimum curve radius of the leg opening areas may be at least about 5 mm, or at least about 10 mm. The contour of the leg opening areas may comprise curved sections of different curve radii.

In any case, the continuous offcut formed by the lateral back portion, main part and lateral front portion may be conveyed away from the process. The present disclosure realizes this conveying away of the offcut in a stable, process-specific, as well as economic manner.

This conveying away is attained with a method of the type mentioned above according to the principles of the present disclosure, in that the offcut is conveyed away by a transfer roller using pin-, needle-, knob-, hook- or barb-shaped mechanical elements protruding from its surface.

A suctioning of the offcut, may at least not be expedient if the area of the offcut is rather limited. The dimensions of the lateral portions in the longitudinal direction of the disposable incontinence diaper are selected such that the offcut, for example, the extension of the web areas of the lateral portions, but also of the main part web to be separated are kept as small as possible. In this case, it is, however, a difficult process to convey the offcut away by means of low-pressure mechanical machine elements from the process. A cutoff composed of different material components may have weak spots in the transition area from one material component to the other which obstructs a process-safe conveying away of the offcuts in a high-speed diaper machine. Therefore, the solution according to the principles of the present disclosure is especially advantageous because it allows a secure gripping of the offcut by the transfer roller and consequently a high process stability by using the above mentioned pin-, needle-, knob-, hook- or barb-shaped mechanical elements in the transfer roller.

The length of the lateral portions, that is, their extension in the longitudinal direction of the diaper, is at least about 15 cm, in particular at least about 20 cm, and furthermore especially at least about 25 cm. It is likewise advantageous, if the length of the lateral portions is at least about 10%, in particular at least about 15%, furthermore especially at least about 20%, and also at least about 22%, in particular, however, at most about 40% and furthermore at most about 35% of the total length of the disposable incontinence diaper. Advantageously, the total length of the disposable incontinence diaper is about 50-120 cm, in particular about 60-110 cm and further in particular about 70-110 cm. It is furthermore advantageous, if the lateral front portions have a shorter length, in particular, a shorter length by at least about 5%, further in particular by at least about 10%, furthermore in particular by at least about 15% than the lateral back portions, and also in particular at most about 50% of said lateral back portions. In another variation of the present disclosure, it is advantageous, if the width of the lateral portions, for example, the extension of the lateral portion beyond the side edge of the main body of the diaper is about 10-45 cm, is in particular about 13-35 cm, furthermore about 15-27 cm. The lateral front portions may have the same width as the lateral back portions. In another variation of the present disclosure, it is advantageous, if the lateral portions may have an area (measured in $cm^2$) that is larger by at least about 15% than the lateral portions.

It is further advantageous, if the lateral front and/or back portions are made of a nonwoven material or comprise a nonwoven material, because such rather voluminous, lofty, three-dimensional nonwoven materials are suitable to be conveyed away as offcuts from the process, compared, for example, to foils.

The nonwovens may contain PE, PP, PET, rayon, cellulose, PA fibers and mixtures of these fibers. Bicomponent or multicomponent fibers are also conceivable and advantageous. Also advantageous are carded nonwovens, spunbonded nonwovens, water needled nonwovens, SM nonwovens, SMS nonwovens, SMMS nonwovens or also laminates made of one or more of these nonwoven types, S standing for spunbonded and M for meltblown nonwoven layers.

According to a further variation of the method according to the principles of the present disclosure, it is proposed that the mechanical elements of the transfer roller provided for gripping the offcut in the area of the lateral back portion and the mechanical elements provided for gripping the offcut in the area of the lateral front portion are configured differently from and/or arranged or oriented differently with respect to the surface of the transfer roller. This different variation and/or different arrangement or orientation, in particular different density of the mechanical elements, that is, different number of mechanical elements per area, or different inclination of the respective mechanical elements with respect to the surface of the transfer roller, may be advantageous for conveying away the offcut, in particular, if the lateral back portions and the lateral front portions are configured differently, that is, in particular differ with regard to at least a primary property selected from the group of type of material, grammage, breathability, density, elasticity, closing force, surface area, thickness or color of the lateral portions and/or the materials. With regard to the primary properties, the designs from EP 07 015 141.0 is fully incorporated herein and are included in the content of the present application. The variation and/or arrangement of the protruding mechanical elements may then be advantageously adapted to the respectively used materials of the lateral front portion and/or lateral back portion in an optimal manner.

In a further variation of the previously mentioned idea of the disclosure, it may prove advantageous, if the mechanical elements of the transfer roller provided for gripping the offcut in the area of the lateral back portion and the mechanical elements of the transfer roller provided for gripping the offcut in the area of the lateral front portion are arranged at an incline in the circumferential direction but in an opposite direction to one another. According to the idea of the disclosure, consideration is given to the fact that the lateral front portion located inside the manufacturing machine in the direction of the web speed may be detached by a relative movement against the direction of the web, and the back portion may be detached by means of a relative movement in the direction of the web. This may, for example, be implemented by minimally decelerating and/or accelerating the transfer roller with respect to the web speed. The above mentioned opposite inclination of the mechanical elements is advantageous for this variation of the detachment process. In this case, the inclination of the mechanical elements is, for example, such that the mechanical elements assigned to the lateral front and/or back portions are inclined toward one another in the circumferential direction.

According to a further concept of the disclosure, in order to detach the offcut from the lateral back portion, the corresponding area of the offcut is gripped and tensioned along the disposable incontinence diaper in the direction of the lateral front portion and/or, in order to detach the offcut from the lateral front portion, the area of the offcut is gripped and tensioned along the disposable incontinence diaper in the direction of the lateral back portion. According to this further idea of the disclosure, a still more certain detachment of the offcut may be guaranteed, even if the separation process has in fact not resulted in a separation along the whole course. During punching or cutting of frequently thin, flimsy web materials, in particular nonwovens or nonwoven/foil bonded materials, there are often situations in which, even after performing an inherently correct web cut, isolated adherent areas, no matter how small they are, remain which cause difficulties in conveying away the offcut. The above mentioned measure may in this case result in additional stabilization of the process.

It may further prove advantageous, if, in order to grip the offcut, a low-pressure support is additionally used in the transfer roller.

It is also advantageous, if the transfer roller is directly arranged downstream of a cutting device for performing the above mentioned continuous or quasi-continuous, single separation process.

Moreover, it is advantageous, if the main part is contoured in the shape of an hourglass during the separation process, while at least the crotch portion of the main part is fitted.

In order to produce a disposable incontinence diaper of the type in question, it is advantageous, if continuous production of the disposable incontinence diaper is provided in the longitudinal direction.

In this regard, a main part web is conveyed in the longitudinal direction, whereby the main part web may comprise a nonwoven material and/or an absorbent body material and/or a backsheet material. The backsheet material may in particular be a foil material or liquid-impervious nonwoven material or a nonwoven/foil laminate.

Moreover, it is advantageous, if a first lateral portion web forming the lateral back portions is conveyed in the longitudinal direction, and a second lateral portion web forming the lateral front portion is likewise conveyed in the longitudinal direction. In this case, the material of the first lateral portion web and the material of the second lateral portion web may differ with regard to at least one of the above mentioned primary properties. Closing means may be attached to the first or second lateral portion web, by means of which the disposable incontinence diaper may be closed in order to be applied to a wearer.

Two first and/or two second lateral portions are conveyed in the longitudinal direction which are advantageously formed during an upstream process step in that a first material web and/or a second material web are longitudinally divided.

First and second portions are then separated from the first and second lateral portion crosswise to the longitudinal direction. The first portions are attached in a synchronized manner to an area of the main body web forming a respective back portion of the disposable incontinence diaper to be produced to form the lateral back portions, and the second portions are attached in a synchronized manner to an area of the main body web forming a respective front portion of the disposable incontinence diaper to be produced to form the respective lateral portions. The distance extending in the machine direction between each front and back portion attached to the main body may be about 110-400 mm, in particular about 200-350 mm. The portions may be attached in a synchronized manner to a continuous nonwoven material web of the main body web, whereby the nonwoven material web forms a side facing the body of the disposable incontinence diaper to be produced.

The continuous or quasi-continuous separation process for contouring the leg opening areas may be implemented, for example as a cutting or punching process. The separation process extends along a separating line which comprises straight and curved sections (referred to the diaper in a flattened state on an even surface). As already described, the separation process includes the lateral back portion, the main part and the lateral front portion in such a way that a one-piece connected offcut is formed.

This offcut 62 (Compare FIG. 5) is thus formed by a section 62a separated from the lateral back portion, by an adjacent section 62c separated from the main part and by an adjacent section 62b separated from the lateral front portion. As already mentioned, these portions are rather limited in area. The section 62a separated from the lateral back portion has the longest extension l1 of 20 to 180 mm, and in particular of 30 to 100 mm. Owing to its curved course, the extension of this section 62a may be much smaller at the transition to the section 62c separated from the main body, and may measure a few millimeters, in particular about 5 to about 30 mm, in particular about 5 to about 20 mm, in particular 5 to 10 mm. Corresponding dimensions l2 apply to the section 62b of the offcut separated from the lateral front portion.

In the longitudinal direction of the disposable incontinence diaper, the extension l3 of the section 62c of the offcut separated from the main part is about 110 to 400 mm, in particular about 200 to about 350 mm; whereas the longest transverse extension l4 of this section 62c separated from the main part is rather short, for example, being about 5 to about 100 mm, in particular about 8 to about 70 mm and furthermore in particular about 10 to about 60 mm. The extension l5 of the offcut 62 in said transverse direction of the disposable incontinence diaper is in particular about 150 to about 350 mm and furthermore in particular about 190 to about 300 mm.

According to a variation according to the principles disclosed, the separation process is implemented such that to detach the offcut from the lateral back portion, the corresponding section of the offcut is gripped and tensioned in the longitudinal direction of the disposable incontinence diaper in the direction of the lateral front portion and/or, that in order to detach the offcut from the lateral front portion, the corresponding section of the offcut is gripped and tensioned in the longitudinal direction of the disposable incontinence diaper in the direction of the lateral back portion.

For example, the separating line follows a constantly differentiable curve, thus not comprising any kinks.

Furthermore, it is advantageous, if the disposable incontinence diaper is produced in such a way that in the case of consecutively conveyed disposable incontinence diapers, the back portion of a disposable incontinence diaper follows the back portion of an adjacent disposable incontinence diaper, and the front portion of a disposable incontinence diaper follows the front portion of an adjacent disposable incontinence diaper.

In a further variation of the principles of the disclosure, it is advantageous, if each first or second section forms lateral portions of two consecutively conveyed disposable incontinence diapers.

Further areas of applicability will become apparent from the description provided herein. It should be understood that the description and specific examples are intended for purposes of illustration only and are not intended to limit the scope of the present disclosure.

DRAWINGS

Figure 2:
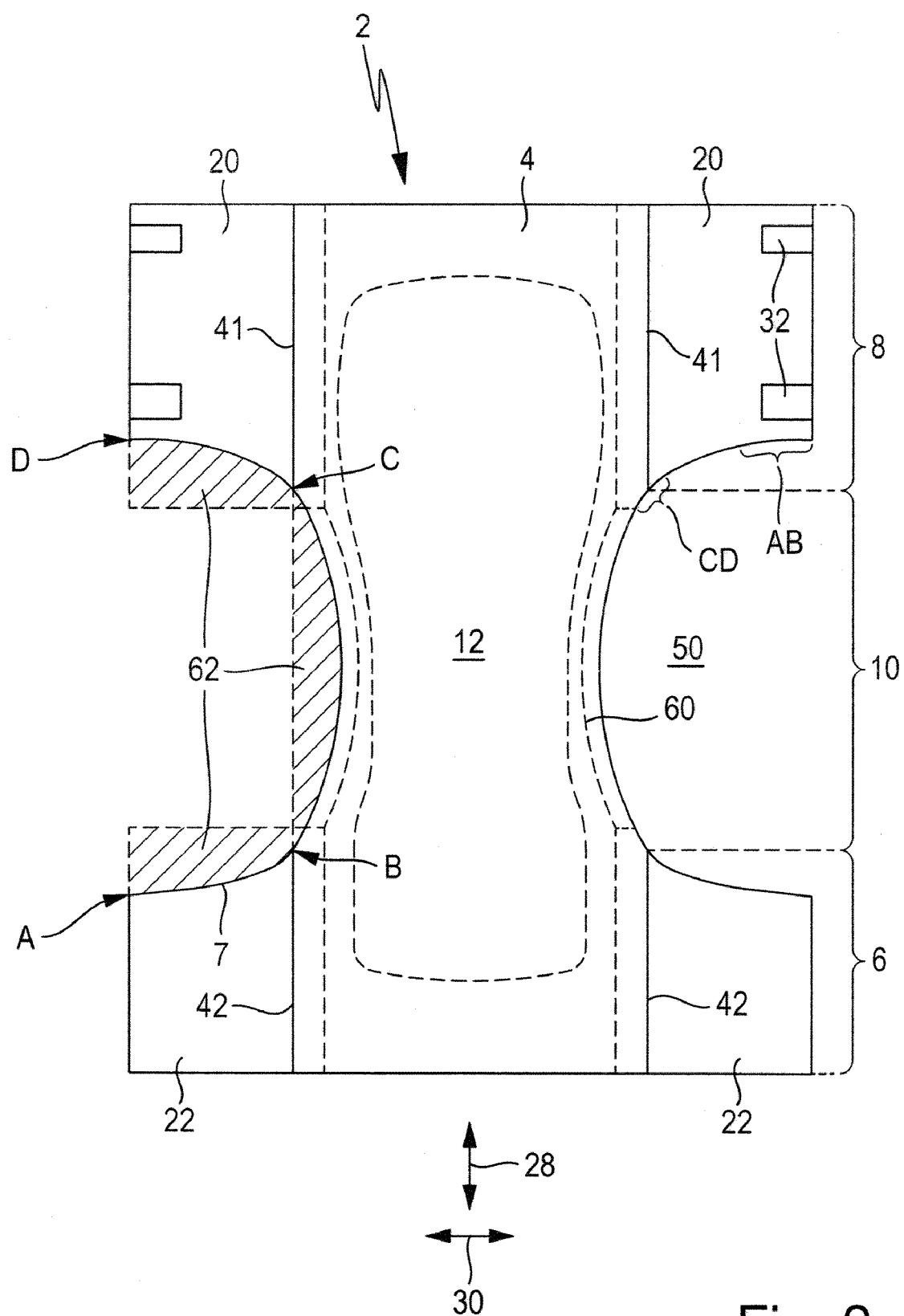
Figure 3A:
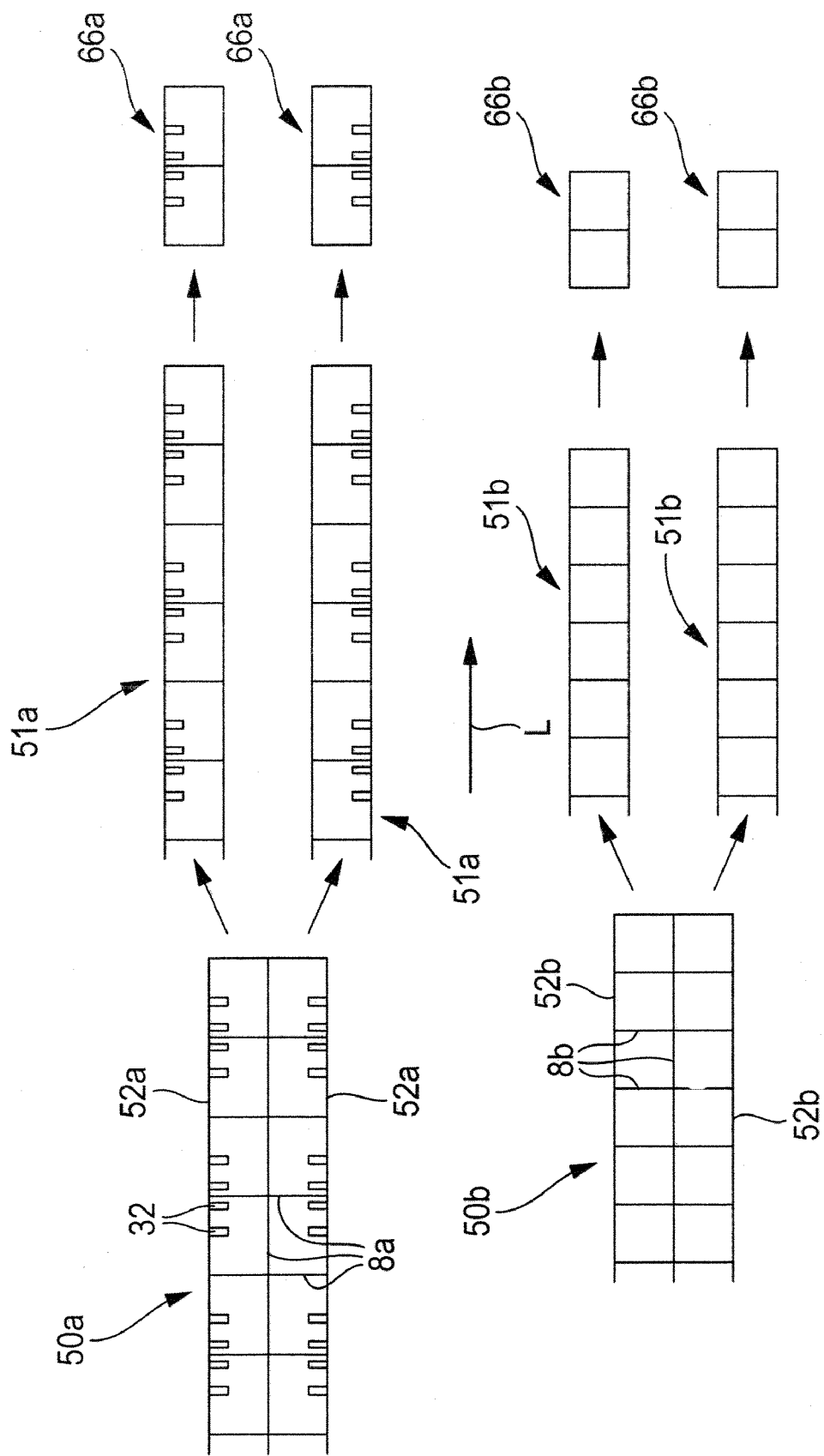
Figure 3B:
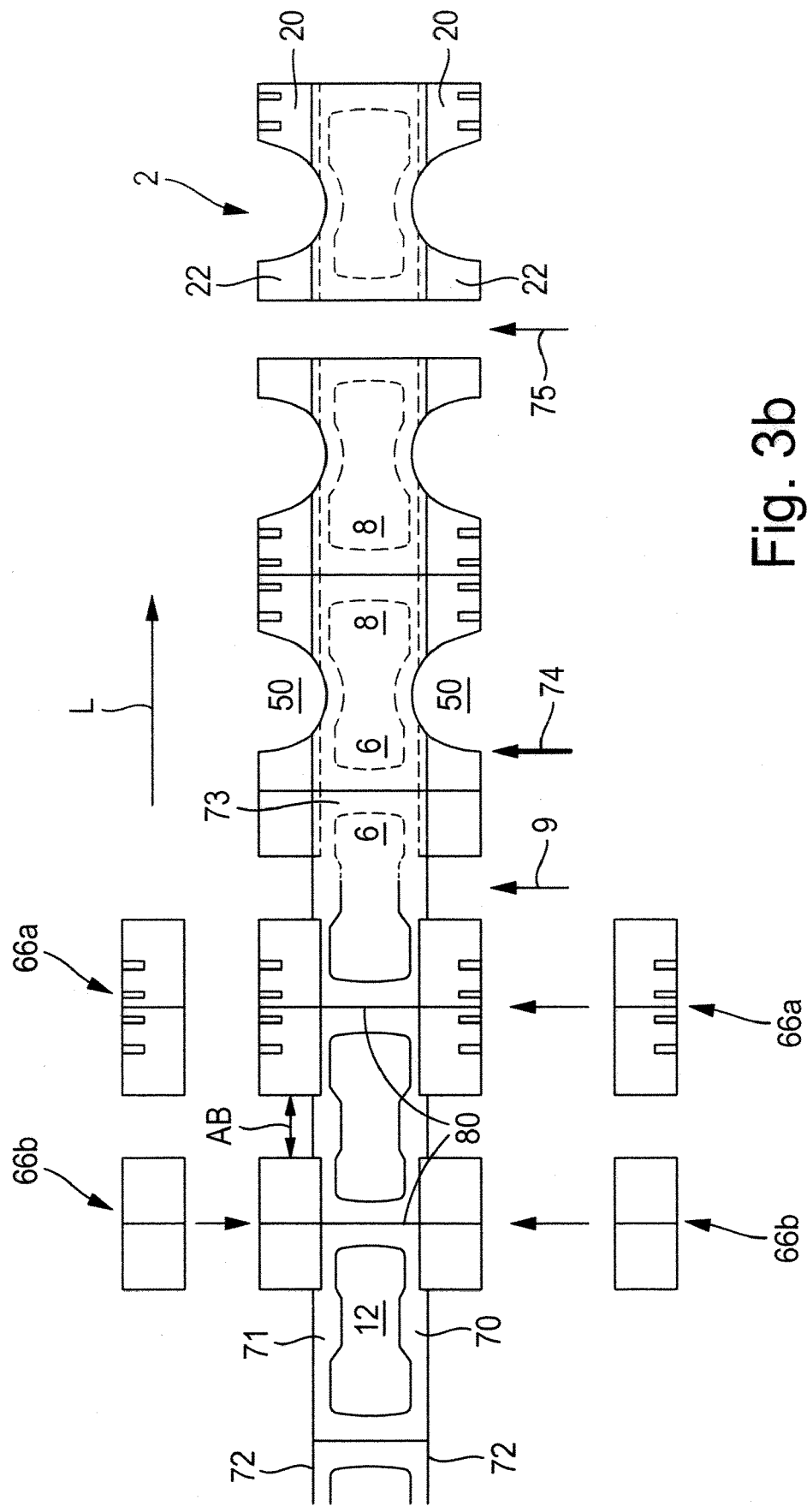
Figure 4:
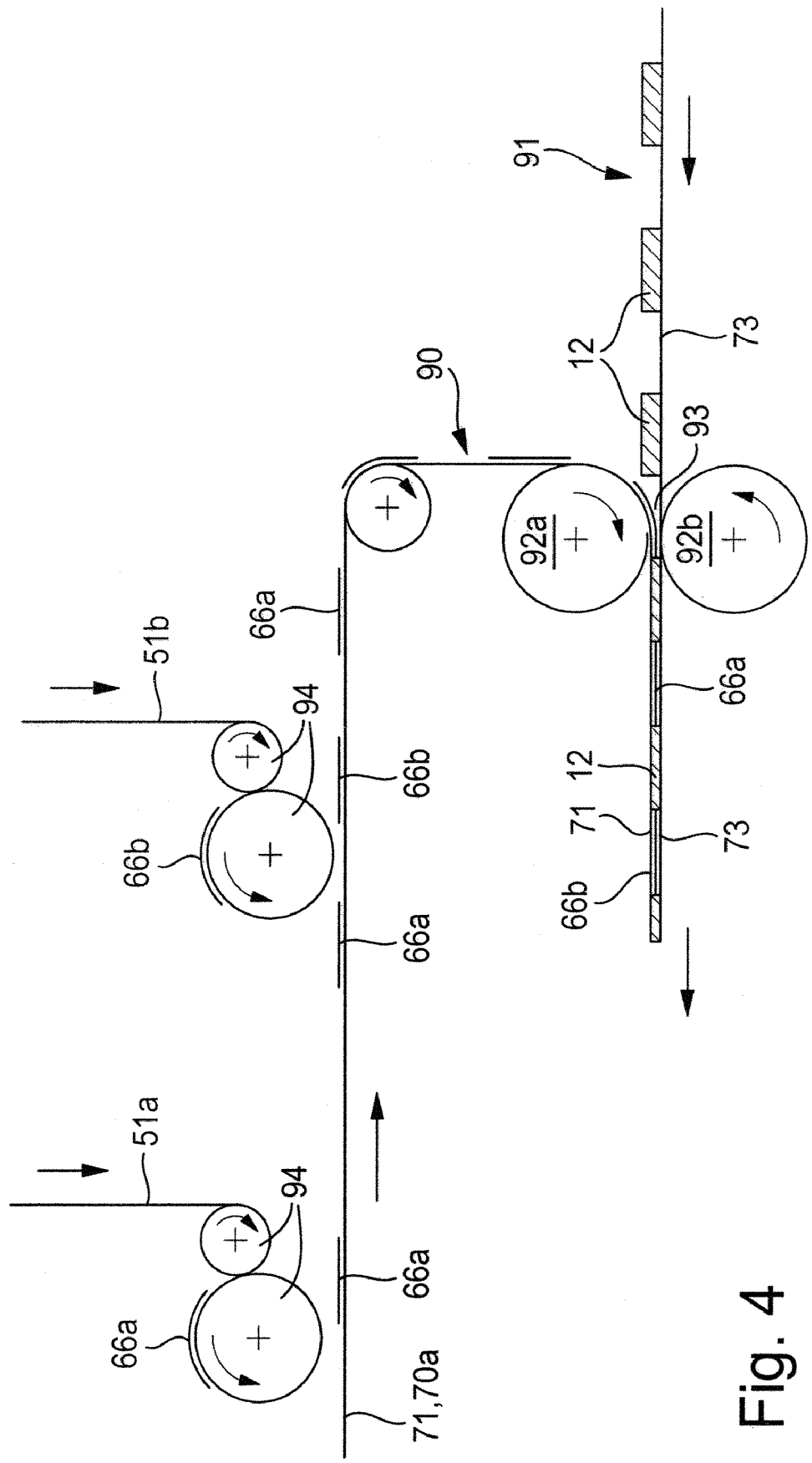
Figure 5:
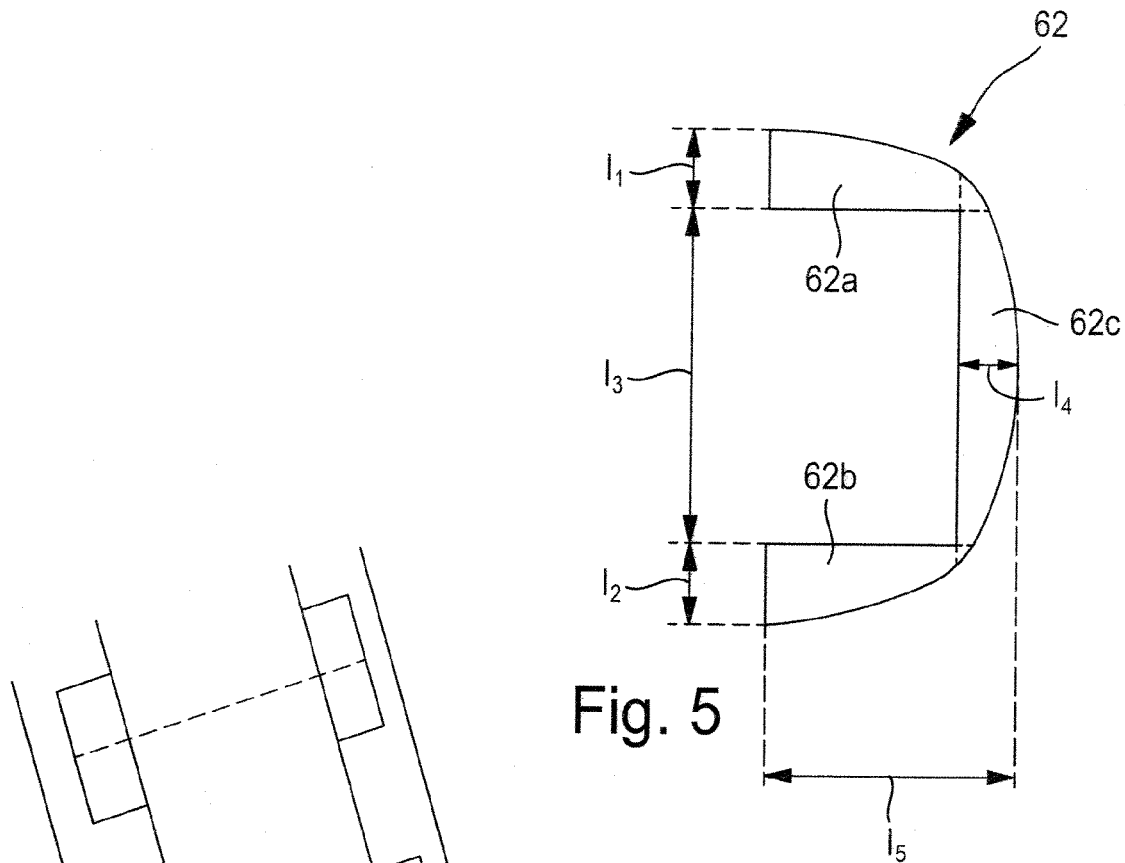
Figure 6:
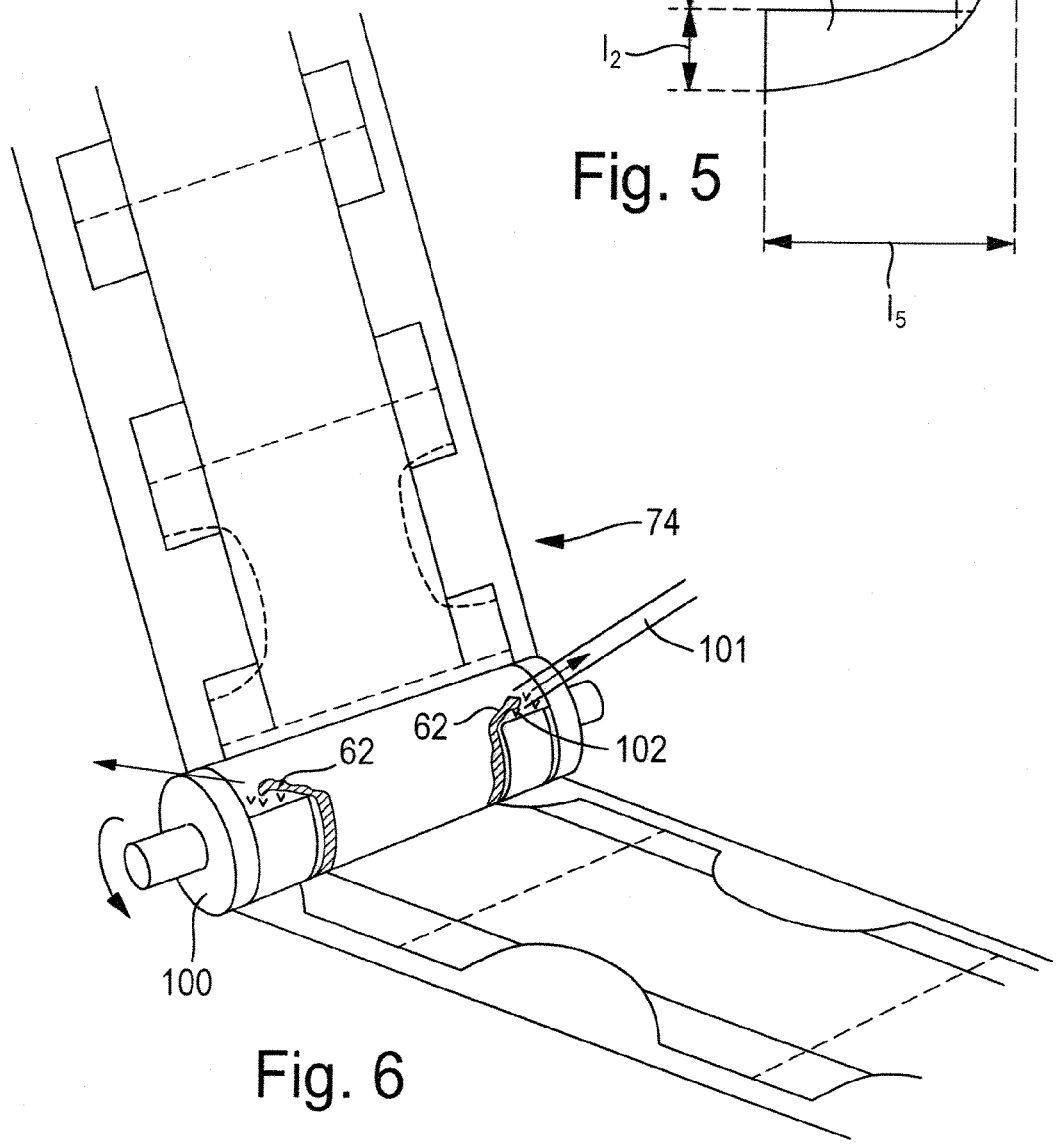
Figure 7A:
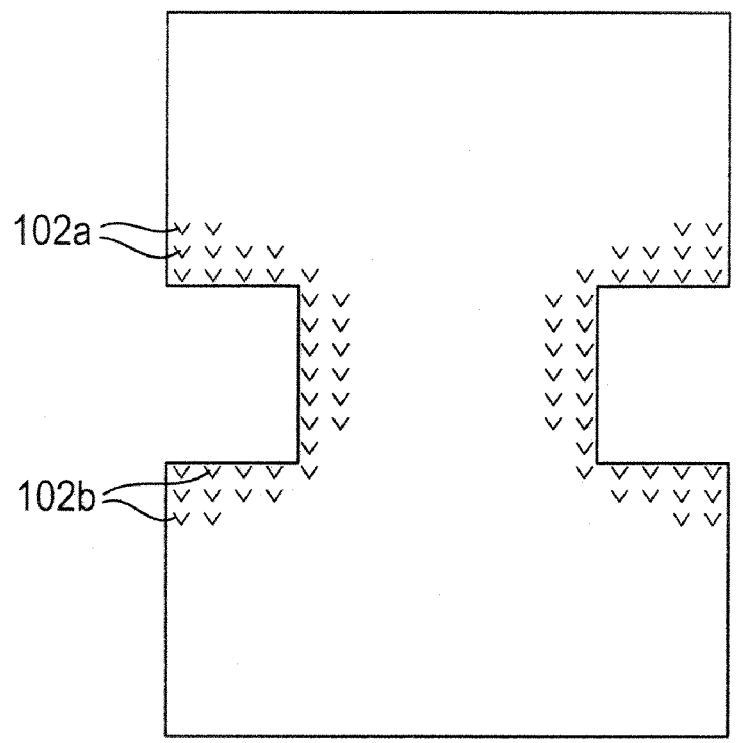
Figure 7B:
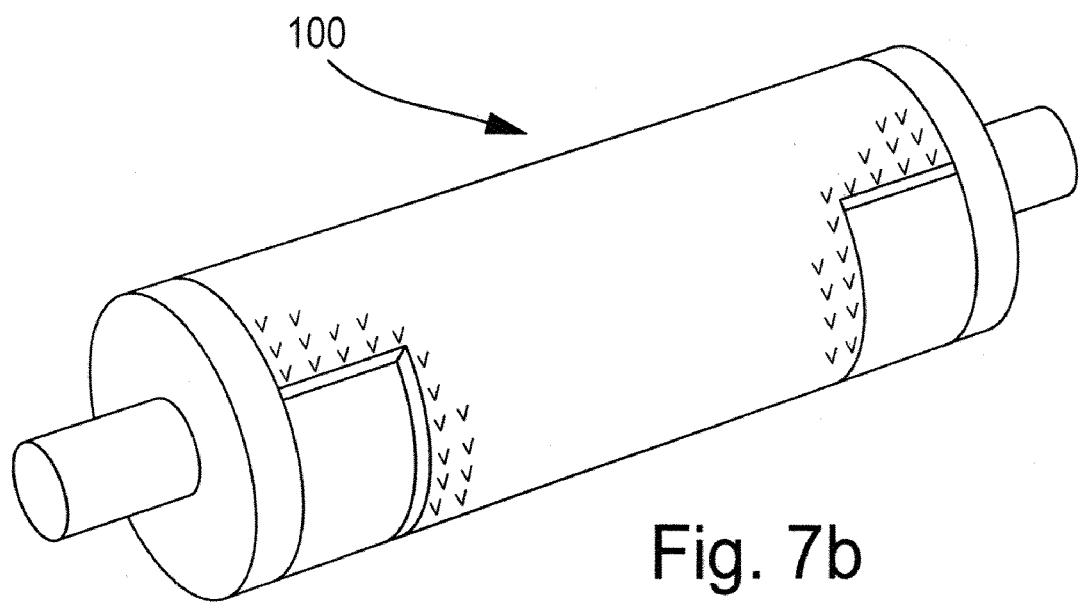
Figure 8:
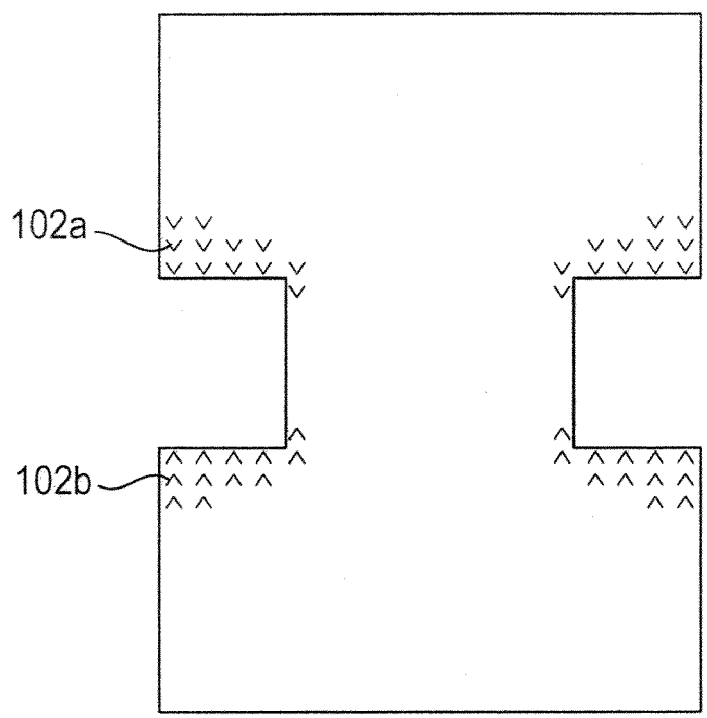

In order that the disclosure may be well understood, there will now be described various forms thereof, given by way of example, reference being made to the accompanying drawings, in which:

FIG. 1: A top view of a disposable incontinence diaper according to the principles of the present disclosure;

FIG. 2: Another top view of the disposable incontinence diaper according to FIG. 1;

FIGS. 3a, 3b: A schematic representation of a production method according to the principles of the present disclosure;

FIG. 4: A schematic representation of production steps of a production method according to the principles of the present disclosure;

FIG. 5: A drawing of a separated offcut;

FIG. 6: A perspective view of the web run over a transfer roller with the above described mechanical elements for the conveying away of the offcut;

FIGS. 7a, 7b: A perspective view of a first variation of a transfer roller for the conveying away of the offcut and a lay-out of the cylinder jacket of the transfer roller;

FIG. 8: A lay-out of a cylinder jacket of a second variation of the transfer roller; and FIG. 9: A lay-out of a cylinder jacket of a third variation of the transfer roller.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

FIG. 1 schematically shows a top view of the inside, that is, a body-facing side, of an absorbent disposable incontinence diaper 2 in a flattened state. The disposable incontinence diaper 2 comprises a main part 4 with a front portion 6, a back portion 8 and a crotch portion 10 placed in-between in the longitudinal direction. Besides, an absorbent body 12 is indicated which is usually arranged between chassis-forming materials of the main part 4, that is, in particular between a liquid-pervious topsheet 11 formed by a nonwoven material and an essentially liquid-impervious backsheet 13 of the main part 4 formed by a foil material. The backsheet 13 may also be formed by a liquid-impervious nonwoven or a nonwoven/foil laminate, the nonwoven layer being then placed on the outside, and the foil layer on the inside with respect to the absorbent body. This provides the disposable incontinence diaper 2 with a textile appearance. Laterally, next to the longitudinal edges of the absorbent body 12, first elastic elements 60 are attached to the main body 4, between the topsheet 11 and backsheet 13. The elastic elements 60 essentially run in the longitudinal direction 28 of the disposable incontinence diaper, that is, with a substantial component in the longitudinal direction 28 whereby they assume a curved course along the section of the leg openings associated with the crotch portion 10. The disposable incontinence diaper 2 also comprises lateral front portions 22 and lateral back portions 20 which are bilaterally attached as separate nonwoven components to the main part 4. The lateral portions 20, 22 are shown in a hatched overlapping area 18 with chassis-forming materials of the main part 4 that is, for example, inseparably connected to the backsheet 13 and/or topsheet 11. The lateral portions 20, 22 extend in the transverse direction 30 beyond the front and back longitudinal edges 42, 41 of the main part. The lateral longitudinal back edges 42, 41 of the main part 4 border those longitudinal edges of the main part to which the lateral portions 20, 22 are attached and over which the lateral portions 20, 22 extend in the transverse direction. The longitudinal extension of the longitudinal front and back edges 42, 41 of the main part 2, 41 thus also defines the longitudinal extension of the front portion 6 and back portion 8 of the main part 4, and also of the disposable incontinence diaper, as shown in FIG. 1. The lateral portions 20, 22 are conceived and designed to be connected to one another in the applied state of the disposable incontinence diaper 2 in order to form a continuous circumferential hip area of the hygiene article. In doing so, each of the lateral portions provided on the side of the main part 4 is connected to one another. For this purpose, mechanical closing means 32 are provided, in particular mechanical closing aids, like stick-on hooks which may be detachably fixed on the outside of the lateral front and back portions 20, 22. The closing means may also be fixed to the outside of the main part 4. The lateral front portions 22, as well as the lateral back portions 20, are formed by a nonwoven material, in the case shown by way of example, by a PP spunbonded nonwoven. The grammage of the nonwoven material of the lateral front portion 22 is 30 g/m². The fiber thickness of the fibers forming the nonwoven material is 2 dtex. The outside and inside of the spunbonded nonwoven have an embossed pattern that is indicated schematically in FIG. 1. The seams produced by means of hot calender embossing are formed by multiple lines, for example, by two groups of respectively parallel lines within each group, the lines of one group intersecting the lines of the other group at an angle of 33 degrees to form a regular diamond pattern, so that diamond-patterned loop areas 15 arranged in an islet-like manner are surrounded by line-like seams 16. In the example shown, the lines forming the seams 16 have a width of 1.0 mm and an embossing depth of 0.6 mm. The distance between two adjacent parallel lines of both groups of lines is 4.7 mm. The embossed area, that is, the sum of the areas of all seams 16 relative to the total area of the embossed pattern (seams 16+loop areas 15) is 32%. The closing means 32 of the back lateral portion 20 may safely be meshed with these loop areas 15. The retention force over the abdomen between the closing means 32 and the outside of the lateral front portion 22 is at least about 58 N/25 mm.

In the case shown, the grammage of the nonwoven material of the lateral back portion 20 is 25 g/m². An embossed pattern forming loop areas and seams is not provided. The retention forces over the abdomen between the closing means 32 and outside of the lateral back portion 20 are therefore smaller than the retention forces over the abdomen between the closing means and the outside of the lateral front portions 22; anyhow, they are at least about 15 N/25 mm, measured according to the test method described in EP 1915977 A1. As is visible in FIG. 1, the lateral back portions 20 in addition have a larger area than the lateral front portions 22.

The lateral front and back portions 20, 22 therefore differ in at least three of their primary properties, for example, the grammage, closing force and area.

The difference in closing force between the front and back portions induces the wearer to, for example, apply the closing means 32 to the lateral front portions 22, which is beneficial for the fit of the diaper. As further indicated in FIG. 1, leg opening areas 50 are formed toward the crotch portion 10 by means of curved front and back lateral portions 20, 22 as well as by means of an hourglass-shaped contouring of the main part 4. Any form of narrowing of the main part 4 in the crotch portion 10 is understood as an hourglass-shaped contouring of the main part 4 in which the crotch portion 10 of the main part 4 has a smaller extension in the transverse direction 30 than the front portion 6 and/or back portion 8 of the main part.

The leg opening areas 50 are each formed by a single cut which includes the lateral portions 20, 22, as well as the main part 4, and is constantly implemented without kinks through the side edge or main part material to be separated. This is even easier to see in the left side view in FIG. 2, which shows the right leg opening area in the applied state. From the previously rectangular, lateral portions 20, 22 and the main part 4 initially provided with straight side edges parallel to one another in the longitudinal direction 28, the offcut 62 shown as hatched has been separated by means of a single curved cut along a separating line or cutting line 7 to achieve the curved course of the lateral portions 20, 22 and of the hourglass-shaped contouring of the main part 4. It may be seen in detail that, starting at a point A at the side edge of the lateral front portion 22, the cutting line 7 initially extends in an inward curve in the direction of the crotch portion 10 to a point B of the longitudinal front edge 42 of the main body 4, then into the main part 4, then further through the crotch portion 10 of the main part 4, and subsequently in an outward curve through a point C of the longitudinal back edge 41 of the main part 4, and finally to a point D at the side edge of the lateral back portion 20. It may be seen that the cutting line is not guided through the absorbent body 12 so that the edges of the absorbent body remain spaced apart from the contour of the leg opening. In the case shown, the contour of the leg opening areas 50 has curved sections, whereby it may be seen that the curve radius is not constant, that is, the leg opening contour does not take a circular shape as a whole, but has sections with different curve radii. Thus, in a section AB, the outer curve radius that reaches to the longitudinal edge of the lateral portion 22, is significantly larger than in the section CD which comprises point C. The curve radius is, however, at least about 5 mm, at least about 10 mm at each point of the leg opening contour. The course of the cutting line 7 is, for example, constantly differentiable, that is, has no kinks.

In order not to overload FIG. 2, the left leg opening area (in the view on the right side of the Figure) is shown in the shape of FIG. 1, that is, without showing the cutting.

FIGS. 3a, 3b schematically show a method according to the principles of the present disclosure for the production of a disposable incontinence diaper shown in FIGS. 1 and 2. FIG. 3a shows the feeding and conveyance process of a first continuous material web 50a in the longitudinal direction of the machine L, whereby the material web 50a has side edges 52a running straight and parallel to one another. Bilateral closing means 32 have previously been attached to this still continuous material web 50a. The position of the imaginary lines of the future separation cuts for forming individual lateral back portions 20 of the disposable incontinence diaper to be produced are provided with the reference numeral 8a. The first material web 50a is in the first instance divided in the longitudinal direction L into two first lateral portion webs 51a. Subsequently, first sections 66a are separated from both lateral portion webs 51a transversely to the longitudinal direction, whereby, as will be described in more detail below, during the course of the production process of the disposable incontinence diapers, sections are respectively separated from each of the lateral portion webs 51a to be attached, either to the left side edge or to the right side edge of the main part web 70.

FIG. 3a also shows the feeding and conveying process of a second continuous material web 50b in the longitudinal direction L, whereby the material web 50b has side edges 52b running straight and parallel to one another. The position of the imaginary lines of the future separation cuts for forming individual lateral front portions 22 of the disposable incontinence diaper to be produced are provided with the reference numeral 8b. The second material web 50b is also initially divided in the longitudinal direction L into the second lateral portion webs 51b. Subsequently, rectangular second sections 66b are separated from both lateral portion webs 51b transversely to the longitudinal direction L which, as will be described in more detail below, are attached to the left, respectively right side edge of a continuous main part web during the further course of the production process of the disposable incontinence diapers. In the case shown, the sections 66a have a larger extension in the longitudinal direction L than the sections 66b.

The first and second rectangular sections 66a, 66b are then fed to a continuous main part web 70 conveyed in the longitudinal direction L, as is visible in FIG. 3b. In the case shown, the main part web 70 comprises a nonwoven material and an absorbent body material, for example, a continuous nonwoven web 71 forming the topsheet, that is, a body-facing side of the disposable incontinence diaper to be produced, with side edges 72 running straight and parallel to one another as well as a continuous number of absorbent bodies 12 consecutively applied and spaced apart from one another. The absorbent bodies 12 contain a mixture of superabsorbent materials (SAP) and fluffed cellulose material. The sections 66a, 66b are fixed for dual use, alternating and on both sides of the nonwoven material, that is, to the lateral longitudinal edges 72 of the main body web 70. In this regard, sections, either to be attached to left longitudinal edge 72 or to its right longitudinal edge 72, are separated from each of the lateral portion webs 51a, 51b. Separation of the sections 66a, 66b from the lateral portion webs 51a, 51b, feeding to the main part web 70, and subsequent attachment of the sections 66a, 66b to both side edges 72 of the main body web 4 are, for example, carried out by means of slip cut or also cut and place units (not shown in FIGS. 3a, 3b). The distance AB extending in the longitudinal direction of the machine between each front and back portion attached to the main part web is about 110-400 mm, in particular about 200-350 mm.

The represented imaginary lines of the future separation cuts 80 that each separated section 66a, 66b forms lateral portions 20, 22 of two consecutively conveyed disposable incontinence diapers 2. For this purpose, the disposable incontinence diapers 2 are produced in such a way that in a disposable incontinence diaper consecutively conveyed in the longitudinal direction L the back portion 8 of a disposable incontinence diaper follows the back portion 8 of an adjacent disposable incontinence diaper, and the front portion 6 of a disposable incontinence diaper follows the front portion 6 of an adjacent disposable incontinence diaper.

After attaching the sections 66a, 66b, a continuous backsheet web 73, in particular a foil web forming the backsheet 13 of the diaper to be produced, is fed to the main part web 70. The backsheet web 73 has a width corresponding to the nonwoven material web, and side edges which likewise run straight and parallel to one another. The backsheet web 73 is fed to the main part web 70 centered from above in an application and joining station, which is schematically indicated with the arrow 9, so that the absorbent bodies are placed between the backsheet web 73 and the nonwoven material web 71, and the backsheet web 73 and the nonwoven material web 71 are directly connected to one another outside the contour of the absorbent bodies 12 by means of a joining method, like bonding, thermal welding or ultrasound welding.

A laminate, in particular a nonwoven/foil laminate web, could also be fed to the main part web 70 as a backsheet web 73. In such cases, the nonwoven layer of the laminate would be arranged outward and the foil facing inward toward the absorbent body 12.

FIG. 3b shows that in the course of the process for the production of the disposable incontinence diapers, the leg opening areas 50 are formed after attaching the sections 66a, 66b and the backsheet web 73 to the main part web 70 to achieve a curved course of the lateral portions 20, 22 and the hourglass-shaped contouring of the main body 4 at both longitudinal sides of the main part web 70 provided with the sections 66a, 66b. This is done by a separation process using a knife roller, which is not shown in a position 74 on each side, by a single continuous cut which, as described in more detail above by means of FIG. 2, is continuously passed through lateral portion or main body material to be separated, so that a constant kink-free course of the cutting line is achieved for contouring the leg opening areas 50.

The offcut 62 formed in the process (See FIGS. 2 and 5) is removed from the production process in a manner according to the present disclosure described below in connection with FIG. 6.

In a further process step shown in FIG. 3b, the still continuous web provided with the leg opening areas 50 is conveyed in the direction of a separation station 75, which is not shown in detail, where a separation cut is essentially carried out transversely to the longitudinal direction L of the machine that corresponds to the longitudinal direction 28 of the disposable incontinence diaper to be produced, for example, likewise by means of a rotating knife roller or a punching tool. The position of the separation cut is indicated in the figures with the reference numeral 80. It is done such that it respectively runs across the applied sections 66a, 66b, that is, the web is transversely separated across the sections 66a, 66b.

In the case that was described and shown in FIG. 3b, the main part web 70 already comprises a composite of the nonwoven material web 71 and absorbent bodies 12 applied thereon at the time of attachment of the sections 66a, 66b.

According to another principle of the disclosure, it would be conceivable, as schematically shown in FIG. 4 as side view, to initially separate the dual-use sections 66a, 66b clocked, in particular by means of so-called slip-cut units 94, from the lateral portion webs 51a, 51b and attach them to both side edges of a main part web 70 which at that time still comprises the nonwoven material web 71 forming the topsheet of the disposable incontinence diaper to be produced. In such cases, this still continuous first composite 90 of the nonwoven material web 72 and sections 66a, 66b is subsequently connected to the other diaper components. In such cases, the still continuous first composite 90 of the nonwoven material web 71 and sections 66a, 66b may be fed to a second composite 91 of a backsheet web 73, in particular to a continuous foil or nonwoven/foil laminate web and to discrete absorbent bodies 12 consecutively applied and spaced apart from one another. The first composite 90 is then bonded to the second composite 91. Bonding the first composite 90 to the second composite 91 could, for example, be carried out by feeding the components to a press and joining nip 93 of a rotating roller pair 92a, 92b, as it is shown in FIG. 4. In this regard, the absorbent bodies 12 are arranged between the backsheet web 73 and the nonwoven material web 71, and the nonwoven material web 71 is directly connected to the backsheet web 73 outside the contour of the absorbent body 12 and bonded therewith. This is then for example, followed by the formation of the leg opening areas 50 and subsequent separation of the disposable incontinence diapers, as described with reference to FIG. 3b (not shown in FIG. 4).

In an alternative process, which is not shown, the first composite could also be fed to a web of discrete consecutive absorbent bodies spaced apart from one another, or these absorbent bodies could be applied in a synchronized manner to the first composite and, if necessary, be fixed onto it. Subsequently, or also nearly at the same time, a backsheet web forming the backsheet of the diapers to be produced, in particular a continuous foil or nonwoven/foil laminate web, may then be fed to the main part web which at that time comprises the first composite of the nonwoven material web and lateral portions as well as the absorbent bodies and connected to the main part web. This is in turn followed by the formation of the leg opening areas and subsequent separation of the disposable incontinence diapers, as described with reference to FIG. 3b.

FIG. 6 schematically shows the web run over a transfer roller 100 for conveying away the offcut which is arranged downstream of the non-depicted knife rollers in the position 74 for contouring the bilateral leg opening areas 50, and by means of which the connected offcut 62 from the lateral back portion 20, main part 4 and lateral front portion 22 may be conveyed away from the process. It may in particular be suctioned off by means of a merely indicated suction device 101 after having been gripped by the transfer roller 100.

FIGS. 7a and b show a perspective view of a first variation of the transfer roller 100 and a lay-out of the jacket of the transfer roller 100. The transfer roller 100 comprises pin-shaped mechanical elements 102 divided into zones for gripping the offcut 62 which protrude from a surface 104 of the transfer roller 100. Mechanical elements 102a are respectively provided which are assigned to the offcut 62 in the area 62a of the lateral back portion 20 and such mechanical elements 102b which are assigned to the lateral front portion 22, and such mechanical elements 102c that are assigned to the offcut 62 in the area 62c of the main body 4 (See FIG. 5).

FIG. 8 shows a second variation of the transfer roller 100 in which the arrangement of the mechanical elements 102 in zones is such that their density (number per area) in the area 62c of the offcut is smaller that in the areas 62a and 62b no mechanical elements at all could even be provided. Besides, the mechanical elements 102 are inclined differently in a circumferential direction to the surface 104 of the transfer roller 100. In the case shown, they are inclined in the opposite circumferential direction but toward one another.

Figure 9:
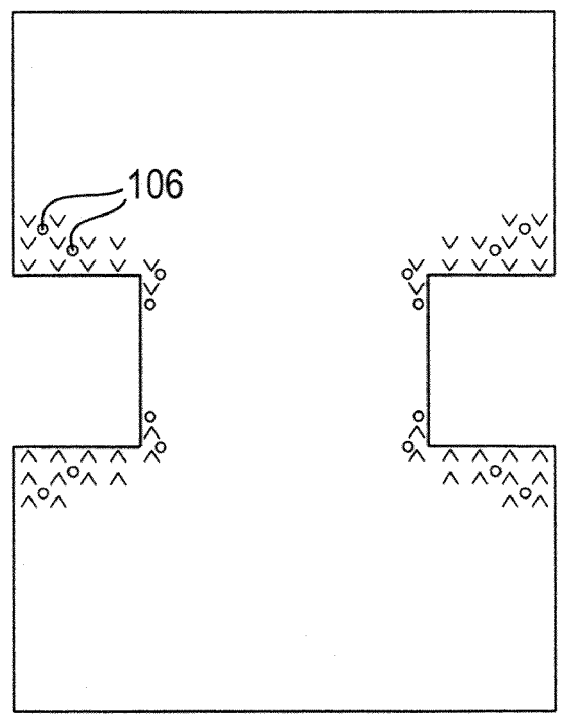

FIG. 9 shows a third variation of the transfer roller 100 in which a low-pressure support is additionally provided in the region of the mechanical elements 102, which is indicated by suction openings 106 that lead to the surface 104 of the transfer roller 100.

The mechanical elements 102,a, b penetrate the material of the offcut 62, for example, in the area 62a of the lateral back portion 20 and/or in the area 62b of the lateral front portion 22, and thus support the gripping of the offcut 62 by the transfer roller 100. To support this gripping of the offcut 62, the transfer roller may be controlled in such a way that, in order to detach the offcut 62 from the lateral back portion 20, the corresponding area 62a of the offcut 62 is tensioned in the longitudinal direction 28 of the disposable incontinence diaper in the direction of the lateral front portion 22, and correspondingly, to detach the offcut 62 from the lateral front portion 22, the corresponding area 62b of the offcut 62 is tensioned in the longitudinal direction 28 of the disposable incontinence diaper in the direction of the lateral back portion 20. This ensures a safe and process-stable conveying away of the offcut 62.

Therefore, the method according to the principles of the present disclosure succeeded for the first time in providing a disposable incontinence diaper with lateral front and back portions attached to the main part, whereby the disposable incontinence diapers have constant leg opening areas, that is, leg opening areas, which are exclusively formed by respective edges resulting of a single continuous or quasi-continuous separation process, so that the disposable incontinence diaper has an excellent fit and a superior wear comfort, besides being process-stable and economic and able to be produced with minimum offcut.

It should be noted that the disclosure is not limited to the variations described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:
1. A method for the production of an absorbent disposable incontinence diaper, with an absorbent body having a main part, comprising a front portion with longitudinal lateral front edges, a back portion with longitudinal lateral back edges and a crotch portion in-between, placed between the legs of the wearer, and with lateral back portions bilaterally attached to the back portion and lateral front portions bilaterally attached to the front portion, which extend in the transverse direction of the disposable incontinence diaper beyond at least one of the longitudinal lateral front and the longitudinal lateral back edges of the main part, and are spaced apart from one another in the longitudinal direction of the disposable incontinence diaper, where the lateral back and front portions may be detachably connected to one another to apply the disposable incontinence diaper, where a continuous or quasi-continuous separation process including the lateral back portion, the main part and the lateral front portion is done to contour the bilateral leg opening areas of the disposable incontinence diaper, so that a connected offcut is formed by the lateral back portion, the main part and the lateral front portion, which has to be conveyed away, characterized in that the offcut is gripped and conveyed away by a transfer roller with at least one of pin-, needle-, knob-, hook- and barb-shaped mechanical elements, the mechanical elements of the transfer roller provided for gripping the offcut in the area of the lateral back portion and the mechanical elements of the transfer roller provided for gripping the offcut in the lateral front portion are at least one of configured differently from and arranged differently with respect to the surface of the transfer roller, and are inclined in the circumferential direction, but in opposite direction to one another.

2. The method according to claim 1 characterized in at least one of that to detach the offcut from the lateral back portion, the corresponding section of the offcut is gripped and tensioned in the longitudinal direction of the disposable incontinence diaper in the direction of the lateral front portion and that in order to detach the offcut from the lateral front portion, the corresponding section of the offcut is gripped and tensioned in the longitudinal direction of the disposable incontinence diaper in the direction of the lateral back portion.

3. The method according to claim 1, characterized in that a low-pressure support is used in the transfer roller to grip the offcut.

4. The method according to one claim 1, characterized in that the transfer roller is arranged downstream of a cutting device.

5. The method according to claim 1, characterized in that the main part is contoured in an hourglass-shape during the implementation of the separation process.

6. The method according to claim 1, characterized in that the disposable incontinence diaper is produced in its longitudinal direction, whereby a main part web is conveyed in the longitudinal direction.

7. The method according to one claim 1, characterized in that a first lateral portion web forming the lateral back portions is conveyed in the longitudinal direction and that a second lateral portion web forming the lateral front portions is conveyed in the longitudinal direction.

8. The method according to claim 1, characterized in that the first and second lateral portion webs differ with regard to at least one primary property selected from the group type of material consisting of grammage, breathability, density, elasticity, closing force, area, thickness, and color.

9. The method according to claim 1, characterized in that first and second sections are separated from the first and second lateral portion web transversely to the longitudinal direction, that the first sections are attached to a region of the main part web forming a respective back portion of the disposable incontinence diaper to be produced to form the lateral back portions, and that the second sections are attached to an area of the main part web forming a respective front portion of the disposable incontinence diaper to be produced to form the lateral front portions.

10. The method according to claim 1, characterized in that the separation process is a cutting or punching process.

11. The method according to claim 1, characterized in that the separation process is guided along a separation line, which comprises at least one of straight and curved sections.

12. The method according to claim 1, characterized in that the disposable incontinence diapers are produced in such a way that with consecutively conveyed disposable incontinence diapers the back portion of a disposable incontinence diaper follows the back portion of an adjacent disposable incontinence diaper, and the front portion of a disposable incontinence diaper follows the front portion of an adjacent disposable incontinence diaper.

13. The method according to claim 12, characterized in that each first or second section forms lateral portions of two consecutively conveyed disposable incontinence diapers.

* * * * *